United States Patent [19]

Lévai et al.

[11] 4,123,615

[45] Oct. 31, 1978

[54] PROCESS FOR PREPARING THE THREO- AND ERYTHRO-ISOMERS OF 1-PHENYL-2-NITRO-1,3-PROPANEDIOL

[75] Inventors: László Lévai; Gyula Mikite, both of Budapest, Hungary

[73] Assignee: Egyt Gyogyszervegyeszeti Gyar, Budapest, Hungary

[21] Appl. No.: 771,369

[22] Filed: Feb. 23, 1977

[30] Foreign Application Priority Data

Feb. 25, 1976 [HU] Hungary .............................. EE 2407

[51] Int. Cl.² ............................................ C07C 76/02
[52] U.S. Cl. ................................. 568/712; 260/570.6; 560/188
[58] Field of Search .................................... 260/618 R

[56] References Cited

U.S. PATENT DOCUMENTS 2,543,957  3/1951  Crooks et al. .................. 260/618 R
3,005,854  10/1961  Braun et al. ..................... 260/618 R Primary Examiner—Joseph E. Evans
Attorney, Agent, or Firm—Young & Thompson

[57] ABSTRACT

The invention relates to a novel process for producing the threo- and erythro-isomers of 1-phenyl-2-nitro-1,3-propanediol through the aldol-type alkaline condensation of benzaldehyde and nitroethanol, wherein the reaction mixture is acidified and, if desired, the isomers are separated from the obtained isomer mixture and the obtained isomers are transformed into each other through epimerization, characterized in that the condensation and, if desired, also the epimerization are carried out in the presence of catalytical amounts of an alkaline hydroxide.

The process according to the invention makes it possible to produce 1-phenyl-2-nitro-1,3-propanediol, an intermediate of the antibiotic chloramphenicol, in high yields, and in an extremely advantageous way which can be carried out simply and economically even on an industrial scale.

10 Claims, 1 Drawing Figure

REACTION SCHEMA 1
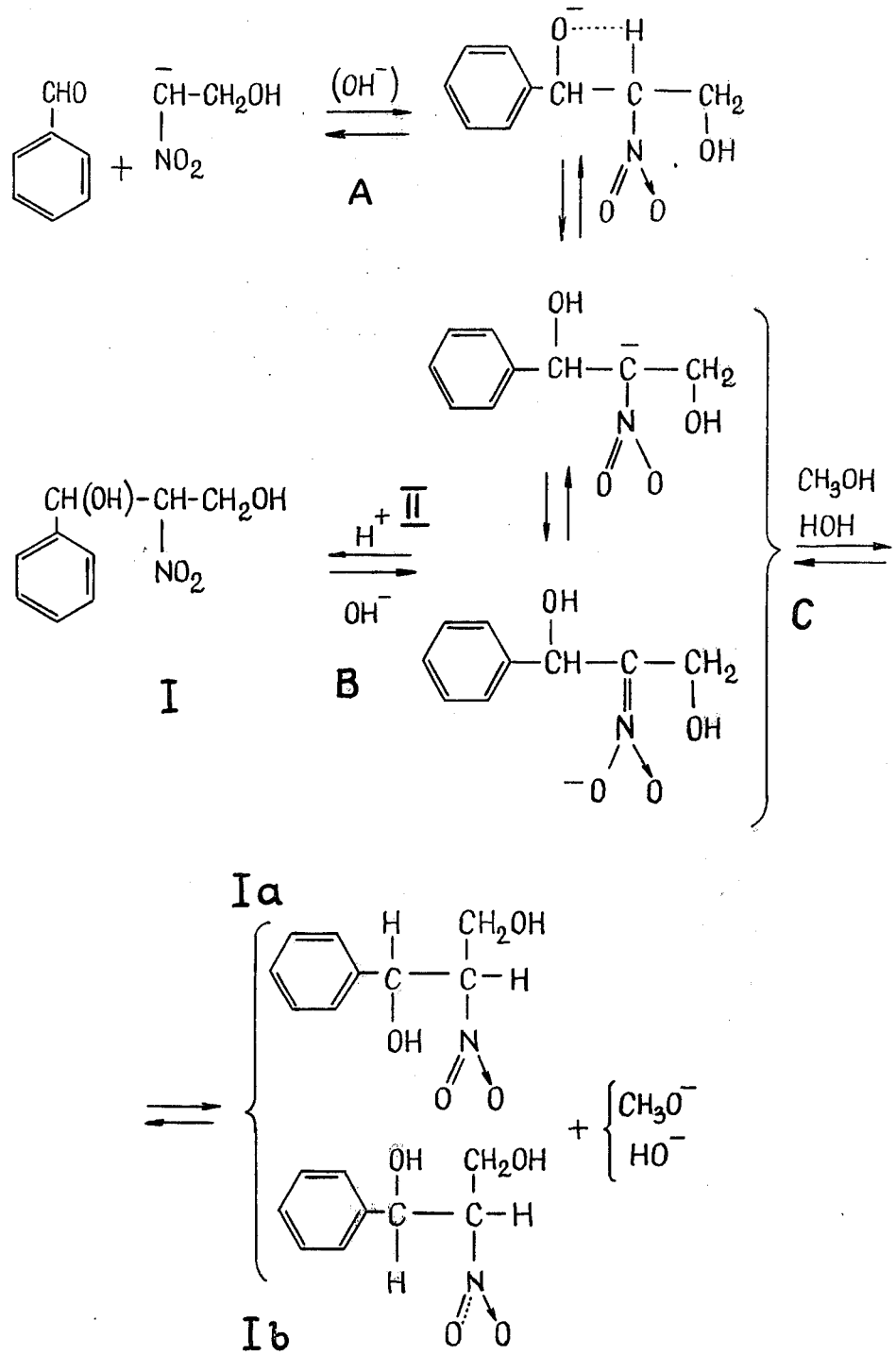

PROCESS FOR PREPARING THE THREO- AND ERYTHRO-ISOMERS OF 1-PHENYL-2-NITRO-1,3-PROPANEDIOL

The invention relates to a novel process for the economic production on an industrial scale of the threo- and erythro-isomers of 1-phenyl-2-nitro-1,3-propanediol. This compound is known in the form of the threo- and erythro-diastereoisomers (herein after: isomers). The threo-isomer is significant in that the important antibiotic known as chloramphenicol can be prepared from it whereas the erythro-compound is the intermediate in the synthesis of other biologically or plant-biologically efficient compounds.

A general method for the preparation of nitroalcohols of this type is the so-called "Henry condensation" (herein after: condensation), a reaction of aldol-condensation type. In this reaction the nitroalcohols are formed from aldehydes and nitroalkanes by means of catalysis induced by bases.

In the literature only one process can be found for the preparation of crystalline threo-1-phenyl-2-nitro-1,3-propanediol (see Reaction Scheme 1, compound of formula I which can be both the threo- and the erythro-compound; in the reaction scheme these two isomers are designated as Ia and Ib). On carrying out this process, the compound is liberated from the sodium salt of 1-phenyl-2-nitro-1,3-propanediol (nitronic acid form; see compound of formula II in Reaction Scheme 1) by the aid of special nitrite-binding agents, such as hydroxylamine, hydrazine etc., avoiding in this way the side reactions which otherwise generally occur with the direct acidification of the salt. The threo-isomer is separated from the threo-erythro isomer mixture by crystallization. Despite the use of the suggested "nitrite-binding agents" and the mild procedure, the yield of the threo-isomer is rather low, only 29.3% (see German Pat. No. 1,064,937). The difficulties encountered in general in the liberation of the nitro-compounds from their salts are otherwise well known from the literature, as also the methods suggested for their prevention (J.A.C.S. 1951, p. 4,041).

The sodium salt itself is prepared (J.A.C.S. 1949, p. 2,465) by the condensation of benzaldehyde and nitroethanol in the presence of stoichiometric amounts of sodium ethylate, with a yield of 67% (see also U.S. Pat. No. 2,483,885).

The above-described synthesis which reflects the present state of the art makes possible after all the preparation of 1-phenyl-2-nitro-1,3-propanediol by a two-step process with low yields. Besides, on considering that the applied "nitrite-binding agents" are expensive, it is clear for any person skilled in the art that these processes are still not developed enough to be suitable to be applied on an industrial scale. Furthermore, no process is known at all for the preparation of the threo-isomer in one step in a high yield.

Accordingly, the invention is a process for producing the threo- and erythro-isomers of 1-phenyl-2-nitro-1,3-propanediol through the aldol-type alkaline condensation of benzaldehyde and nitroethanol, wherein the reaction mixture is acidified and, if desired, the isomers are separated from the obtained isomer mixture and, respectively, the obtained isomers are transformed into each other through epimerization, characterized in that the condensation and, if desired, also the epimerization are carried out in the presence of catalytical amounts of an alkaline hydroxide.

Potassium hydroxide is preferably used as alkaline hydroxide and methanol is preferably used as a lower alkanol.

The condensation is preferably carried out in a lower alkanol as reaction medium, in the temperature interval ranging from −25° C. to +10° C.

According to another preferred method of the invention the reaction is carried out in an aqueous medium containing a lower alkanol in an amount of at most 25% by weight, in the temperature interval ranging from −10° C. to +10° C.

The novel process according to the invention is a catalytic method in which only a fraction of the stoichiometric amount of the base is used for the condensation of benzaldehyde and nitroethanol. The use of a catalyst in this method results in advantages which are a priori excluded in case of non-catalytic processes. As it will be shown further on, this catalytic process correlates in the case of the preparation of the threo-isomer to a stereoselective reaction. With the erythro-isomer this result can be attained only in several steps. By means of the process according to the invention the important 1-phenyl-2-nitro-1,3-propanediol can be produced advantageously even on a large industrial scale.

When after the termination of the condensation reaction the reaction mixture is acidified, the alcohol is removed by distillation, the solid residue is mixed with water, and the thus-obtained threo-erythro-isomer mixture is extracted with a solvent followed by evaporation of the solvent. On crystallizing the isomer mixture 50% crude erythro-isomer is isolated as a thick syrup beside 45% of crystalline threo-isomer.

This obtained syrup contains about 82% of erythro-isomer contaminated mainly with threo-isomer. Consequently the real yield of the erythro-isomer is 41%.

On epimerization (see Reaction Scheme 1, reaction B) the erythro product or, if desired, the threo product is carried back essentially into the conditions of the condensation, i.e. treated in the above-specified way with catalytical amounts of an alkaline hydroxide. On processing in a way identical with that described above, a mixture of threo- and erythro- isomers is obtained, from which, beside 50% of crude erythro-isomer, also here 45% of crystalline threo-product can be isolated.

Thus the combined yield of condensation and epimerization amounts to 63.4% (referred to benzaldehyde) which can be further increased to 69.5% by a repeated epimerization.

When the erythro product is to be prepared, then the threo product formed beside the erythro-product in a practically equivalent amount is epimerized to an isomer mixture, from which the three-isomer is allowed to crystallize, and a further amount of the erythro product is isolated from the mother liquor.

The epimerization of the other isomer can be carried out according to the invention by adding this isomer to a new batch of benzaldehyde and nitro- ethanol to be condensed.

When the threo-isomer is to be prepared, benzaldehyde is allowed to react with nitroethanol in the presence of catalytical amounts of an alkaline hydroxide in an aqueous medium, to which, if desired, an agent depressing the freezing point, such as an alcohol, preferably methanol, is added at a temperature between +10° C. and −10° C.

From the reaction mixture the threo-1-phenyl-2-nitro-1,3-propandiol isomer precipitates. After the termination of the reaction, when the precipitation of the threo product is ended, the reaction mixture is adjusted with an acid preferably stepwise to an acidic pH value, and the crystalline product is filtered off or isolated by extraction with a solvent followed by evaporation of the solvent. The primary yield is 64 to 73% of threo-isomer which can be raised to 73 to 80% by the epimerization of the secondary product obtained from the mother liquor.

In the above condensation reactions the amount of base applied as catalyst is only a minor fraction of the stoichiometric amount; e.g. in case of using potassium hydroxide only one fifth of the stoichiometric amount is actually applied. In the case of base amounts essentially higher then this value the yield decreases. During epimerization the optimum amount of catalyst is slightly higher (at about two fifths of the stoichiometric amount) which is due to the fact that it is more difficult to deprotonate the nitrodiol of formula (I) than the nitroethanol.

The pH range advantageous for the reaction is above 10.

The extraction of nitrodiols can be carried out with various solvents, such as ethyl acetate, butyl acetate, ether and their benzolic mixtures. For the crystallisation of the isomers the chlorinated hydrocarbons, e.g. chloroform, are particularly suitable in which the threo-isomer is practically insoluble whereas the erythro-isomer is readily soluble.

The reaction time is about 30 minutes when condensation and epimerization are carried out as separate steps whereas in the case of preparing the threo-isomer it is longer, amounting to about 3–4 hours.

For the acidification of the reaction mixture inorganic and organic acids are equally suitable. When required by further preparative tasks, the crude erythro product can be purified in a simple way by shaking with a 10% aqueous sodium hydrogen sulphite solution in a solvent, e.g. in chloroform (at 0° C.) and subsequent evaporation of the solvent. The product purified in this way is a viscous oil.

The erythro structure has been converted by hydrogenation into erythro-1-phenyl-2-amino-1,3-propanediol (m.p. 104° to 105° C.) and acetylation into the hitherto unknown erythro-1-phenyl-2-nitro-1,3-diacetoxypropane (m.p. 81° C.).

According to what has been said above, the claimed process consists essentially in a condensation and an epimerization carried out under catalytic conditions, wherein the two reactions take place either in two consecutive steps or, when the threo isomer is to be prepared, they are carried out in one step simultaneously.

The essential principle of the invention can be readily understood from the following reaction mechanism.

As it appears from Reaction Scheme 1, the condensation (reaction A) and epimerization (reaction B) take place according to a single mechanism of reaction, on the basis of the general principle of catalyses by base. Consequently, in the equilibrium mixture the ratio of the threo- and erythro-isomers must be the same in both reactions. Namely, in the tautomeric equilibrium system combining condensation and epimerization the common nitronate anion of formula II is formed which is in equilibrium also with the regular nitro compound (threo- and erythro-isomers) (reaction C). Due to the fact that all the molecules participate in this equilibrium, i.e. they pass the stage of nitronate anion, and because the formation of both isomers is determined by the protonation of this anion, the percentual distribution of the threo-erythro isomers will be the same value both in condensation and in epimerization, as also proved by our own experience. The accurate value of the distribution of isomers can be given in the knowledge of the threo-contamination of the erythro-isomer since this latter is always contaminated by the threo-isomer. According to our experiments this value corresponds to a threo-erythro ratio of about 1:0.9. Surprisingly, in contrast to the accepted relevant theories, in the present case the thermodynamical stability of the threo-isomer appears to be higher than that of the erythro-isomer.

In the case of preparing the threo-isomer, owing to the insolubility in water of the threo-isomer, this isomer precipitates from the primary threo-erythro isomer mixture formed in the condensation (reaction A) whereas the erythro-isomer is at the same time epimerized by the effect of the base again to an equilibrium mixture of the threo- and erythro isomers (reaction B). From this latter mixture the threo-isomer precipitates again, and this process is continued until the entire amount is converted into threo-isomer.

This feature of the claimed process represents a special and rarely occurring reaction type which in respect to its character stands nearest to the conversion known as "secondary asymmetric transformation". In these latter processes the nearly quantitative conversion of the diastereomers of a racemic compound into one of the active components becomes possible also by epimerization and simultaneous crystallization of one of the epimers.

This variant of the process according to the invention can be considered as a stereoselective reaction from the aspect of the "overall" process provided that the partial processes are not taken into account.

The process according to the invention is further illustrated by the aid of the following Examples.

EXAMPLE 1

To a mixture of 10.6 g. (0.1 moles) of freshly distilled benzaldehyde, 10.0 g. (0.11 moles) of nitroethanol and 18 ml. of methanol, cooled to −8° C., a solution of 1.1 g. of potassium hydroxide in 12 ml. of methanol cooled also to −8° C. is added in 10 minutes under stirring, and the stirring is continued at the same temperature for a further 30 minutes. Then at −10° C. a solution of 1.5 ml. of acetic acid in 4 ml. of methanol is at once poured into the mixture, and the stirring is continued at this temperature for 25 minutes. On removing methanol from the reaction mixture in a rotated evaporator in vacuo at a temperature not exceeding 35° C., 24.0 g. of a viscous product is obtained which is dissolved in a cold (0° to +5° C.) mixture of 30 ml. of water and 40 ml. of diethyl ether, then the pH is adjusted with sodium hydrogen carbonate to a value of 7, and the ethereal phase is separated from the aqueous phase. The aqueous phase is extracted twice with ether, the combined ethereal phases are dried with magnesium sulphate, evaporated in vacuo in a rotated evaporator, and the residual viscous mass is seeded at the end of the distillation with threo-1-phenyl-2-nitro-1,3-propanediol. After about 30 to 60 minutes the whole mass of the product is crystallized. The product obtained in this way weighs 20.15 g. and contains a mixture of the threo- and erythro-isomers.

Subsequently the thus-obtained substance is suspended in a mixture of 16 ml. of chloroform and 5.9 ml.

of petroleum ether, allowed to stand overnight in a refrigerator and then for 2 hours more at −8° C. On filtration, washing with 8.5 ml. of cold chloroform, and careful drying, the yield is 8.85 g. of the threo-isomer (45%); m.p. 91°-92° C.

For the epimerization the chloroformic mother liquor of crystallization is used, the evaporation of which (in vacuo at a temperature below 35° C.) affords 9.8 g. (50%) of crude erythro-isomer (a product of a nitrodiol content of about 82%). This product is dissolved in 9.0 ml. of methanol cooled to −8° C., then a solution of 1.0 g. of potassium hydroxide in 22.4 ml of methanol cooled similarly to −8° C. is added in 10 minutes under stirring. Stirring is continued for a further 30 minutes at −8° C. Subsequently at −10° C. a solution of 1.61 ml. of glacial acetic acid in 5.31 ml. of methanol is at once added and stirring is continued at this temperature for 25 minutes. Evaporation in vacuo carried out in a way similar to that described above affords 13.46 g. of product which is dissolved in a cooled mixture of 10 ml. of distilled water and 30 ml. of diethyl ether. On adjusting the pH of the medium with sodium hydrogen carbonate to a value of 7, the ethereal phase is separated, the aqueous phase is repeatedly extracted with ether, and the combined ethereal phases are evaporated in the usual way, affording 9.66 g. of a crude isomer mixture. On crystallization in the above-described way (chloroform, petroleum ether), the yield of the threo-isomer is 3.62 g. (45%); m.p. 91°-92° C.

By the evaporation of the mother liquor 5.0 g. of crude erythro-isomer is obtained from which, by epimerization or more simply by returning it to a new condensation, further amounts of the threo-isomer can be recovered (1.2 g /6.2%/; m.p. 91°-92° C.), raising the overall yield to 13.67 g. (69.5%).

EXAMPLE 2

To a solution of 15.0 g. of threo-1-phenyl-2-nitro-1,3-propanediol in 15 ml. of methanol at −8° C., a solution of 1.68 g. of potassium hydroxide in 37.5 ml. of methanol cooled to −8° C. is added dropwise at the same temperature.

Stirring is continued for 30 minutes at −8° C. The reaction mixture is acidified at −10° C. with a solution of 2.7 ml. of acetic acid in 9 ml. of methanol and the mixture is stirred for 25 minutes at this temperature. On evaporating the mixture in vacuo, the formed residue of 20.77 g. is dissolved in a mixture of 22.5 ml. of distilled water and 30 ml. of diethyl ether at 0° C. The pH of the solution is adjusted to a value of 7 with sodium hydrogen carbonate, and the ethereal phase is separated from the aqueous phase. On extracting the aqueous phase twice with ether, the combined ethereal phases are dried with magnesium sulphate and evaporated. On seeding with the threo-isomer at the end of the evaporation, crystallization starts. On crystallizing the thus-obtained 14.65 g. of isomer mixture, the yield of threo-isomer is 6.59 g. (44%); m.p. 88°-89° C.

The erythro-isomer is obtained by evaporation of the mother liquor with a yield of 6.4 g. (42.6%).

EXAMPLE 3

A mixture of 21.2 g. (0.2 moles) of benzaldehyde, 18.2 g. (0.2 moles) of nitroethanol and 60 ml. of water is cooled to −5° C., then a solution of 3.2 g. of potassium hydroxide in 5 ml. of water is added under stirring. After stirring at −4° C. for about an hour, the substance begins to precipitate. Then 4 ml. of methanol are added, and stirring is continued at the same temperature for 3 hours. Carbon dioxide gas is introduced into the solution until the pH value decreases to about 7.5. Subsequently a mixture of 5 ml. of acetic acid and 5 ml. of water is dropwise added in 20 minutes. The precipitated crystals are filtered, washed twice with 20 ml. of icy 0.1 N hydrochloric acid, then twice with 20 ml. chloroform. Yield: 25.3 g. (64.5%); m.p. 86°-90° C.

Processing of the mother liquor: After the separation of the chloroformic phase, the aqueous phase is extracted thrice with 10 ml. portions of ethyl acetate, the extracts are combined with the chloroformic phase, dried on magnesium sulphate and evaporated. To the residual 12 g. of oil 12 ml. of chloroform are added, and the mixture is allowed to stand overnight in a refrigerator, then filtered, and the crystals washed twice with 3 ml. portions of chloroform. Yield: 3.12 g. (7.94%); m.p. 88°-91° C.

On evaporating the mother liquor 7.0 g. of a viscous residue are obtained which are used for epimerization.

Purification: The threo-isomers prepared as specified above are combined (28.4 g.), stirred at room temperature for 4 hours in a mixture of 50 ml. of water and 1 ml. of concentrated hydrochloric acid, then filtered and washed twice with 15 ml. portions of chloroform.

The overall yield of the condensation is 22.4 g. (56.8%); m.p. 92°-93° C. Combined with a further 2.64 g. of product having a melting point of 93° to 94° C. and obtained by extracting the mother liquor, the yield is raised to 25.4 g. (63.5%).

On evaporating this final mother liquor obtained after the extraction, a further 3 g. of epimerizable product are recovered.

10 g. of the mother liquor product are stirred with a mixture of 10 ml. of water, 8.0 ml. of methanol and 1 g. of potassium hydroxide at −5° C. for 30 minutes, acidified in 20 minutes with a solution of 1 ml. of acetic acid and 5 ml. of water, then the pH of the medium is adjusted with a 1:1 diluted mixture of concentrated hydrochloric acid and water to a value of 2. The solution is extracted thrice with 6.0 ml. portions of ethyl acetate, dried on magnesium sulphate and evaporated. The residual 8.5 g. of viscous oil are mixed with 8 ml. of chloroform and allowed to stand overnight, then the precipitated crystals are filtered. Yield: 1.2 g. (3.0%) of threo-isomer; m.p. 90°-92° C.

The overall yield of condensation and epimerization amounts to 66.5%.

EXAMPLE 4

A solution of 3.2 g. of potassium hydroxide in 5 ml. of water is dropwise added to a mixture of 21.2 g. (0.2 moles) of benzaldehyde and 18.2 g. of nitroethanol (0.2 moles) in 50 ml. of water cooled to −5° C. On adding 0.2 g. of Arcopon-T emulsifier and 5 ml. of methanol to the reaction mixture, it is stirred at −4° C. for 3 hours. In order to acidify the mixture at first a solution of 3 ml. of acetic acid in 5 ml. of water is dropwise added in 20 minutes, then a solution of 3 ml. of concentrated hydrochloric acid in 6 ml. of water is added similarly dropwise in 20 minutes. The reaction mixture is extracted thrice with 15 ml. of ethyl acetate, dried on magnesium sulphate and evaporated in vacuo, affording 39 g. of an oil which is stirred with 39 ml. of chloroform at 0° C. for 4 hours, then the crystalline precipitate is filtered.

Yield: 23.5 g. (59.7%); m.p. 92°-93° C.

Epimerization: By epimerizing in the way specified in Example 3 the 14.5 g. of oil obtained by the evaporation of the above-mentioned mother liquor of crystallization, the yield is 3.2 g. (8.12%); m.p. 92°–93° C.

Overall yield: 67.82%.

EXAMPLE 5

A mixture of 21.2 g. (0.2 moles) of benzaldehyde, 18.2 g. of nitroethanol and 50 ml. of water is cooled to −5° C., and a solution of 2.4 g. of potassium hydroxide in 5 ml. of water, and a further 5 ml. of ethanol are dropwise added, then the mixture is stirred at −4° C. for 3 hours. The reaction mixture is acidified (to pH 2) in 45 minutes with 10 ml. of a 1:1 mixture of concentrated hydrochloric acid and water. The solution is extracted thrice with 15 ml. portions of ethyl acetate, whereafter the combined extracts are dried on magnesium sulphate and evaporated in vacuo, affording a residue of 40.2 g. which is crystallized from 40 ml. of chloroform. Yield: 23.78 g. (60.3%); m.p. 92°–93° C.

The oily product of 14.35 g. obtained on the evaporation of the mother liquor is used in the next experiment.

EXAMPLE 6

Condensation is carried out in the way specified in Example 5, with the difference, however, that after the addition of the base also the 14.35 g. of residue mentioned at the end of Example 5 are added to the reaction mixture. The mixture is processed as in Example 5. The primary epimer mixture weighs 50.8 g., yielding by means of the usual crystallization 27.6 g. (70%) of the product; m.p. 93°–94° C.

On epimerizing the mother liquor, a further 2.43 g. (6.25%) of threo-isomer of m.p. 92°–94° C. are obtained.

Total yield: 76.25%.

EXAMPLE 7

A mixture of 9.1 g. (0.1 moles) of nitroethanol, 9.6 g. (0.09 moles) of benzaldehyde, 25 ml. of water and 2 ml. of methanol is cooled to −5° C., then a solution of 1.4 g. of potassium hydroxide in 2.5 ml. of water is added, the mixture is stirred at −3° C. for 2.5 hours and acidified with a mixture of 2.5 ml. of acetic acid and 2.5 ml. of water added at once. After stirring the mixture for 30 minutes, it is extracted with 20 ml. of ethyl acetate, dried and evaporated, affording 19.7 g. of an oil which on crystallization from 20 ml. of chloroform gives:

I. 13.1 g. of threo-isomer
  (yield referred to nitroethanol: 66.5%;
  referred to benzaldehyde: 73.5%);
  m.p. 90°–91.5° C.

On evaporating the chloroformic mother liquor and isomerizing the obtained 5.6 g. of oil:

II. 1.8 g. of crystalline product are obtained
  (yield referred to nitroethanol: 9.15%;
  referred to benzaldehyde: 10.20%).

Purification: Products I + II are stirred with 1 drop of concentrated hydrochloric acid and 20 ml. of chloroform at 20° C. for 6 hours, then filtered and dried.

Yield: 14.2 g. (referred to nitroethanol: 72%;
referred to benzaldehyde: 80%);
m.p. 93°–94° C.

What we claim is:

1. A process for producing the threo- and erythro-isomers of 1-phenyl-2-nitro-1,3-propanediol in the form of the free nitrodiol in crystalline form, through the aldol-type alkaline condensation of benzaldehyde and nitroethanol and acidifying the reaction mixture, characterized in that the condensation is carried out in the presence of a catalytical amount of an alkaline hydroxide which is only a minor fraction of the stoichiometric amount.

2. A process as claimed in claim 1, characterized in that after acidifying the reaction mixture the isomers are separated from the obtained mixture of the isomers.

3. A process as claimed in claim 2, characterized in that the obtained isomers are transformed into each other through epimerisation carried out in the presence of a catalytical amount of an alkaline hydroxide which is only a minor fraction of the stoichiometric amount.

4. A process as claimed in claim 1, characterized in that potassium hydroxide is used as alkaline hydroxide.

5. A process as claimed in claim 1, characterized in that the condensation reaction is carried out in a lower alkanol as reaction medium, in the temperature interval ranging from −25° C. to +10° C.

6. A process as claimed in claim 1, characterized in that the condensation reaction is carried out in an aqueous medium containing a lower alkanol in an amount of at most 25% by weight, in the temperature interval ranging from −10° C. to +10° C.

7. A process as claimed in claim 1, characterized in that methanol is used as lower alkanol.

8. A process as claimed in claim 5, characterized in that methanol is used as lower alkanol.

9. A process as claimed in claim 1, in which said fraction is about one-fifth.

10. A process as claimed in claim 3, in which the last-named fraction is about two-fifths.

* * * * *